United States Patent
Fasoli

(10) Patent No.: US 9,480,440 B2
(45) Date of Patent: Nov. 1, 2016

(54) SYSTEM AND METHOD FOR CONE BEAM COMPUTED TOMOGRAPHY

(75) Inventor: Martino Fasoli, Verona (IT)

(73) Assignee: QR SRL, Bologna (IT)

(*) Notice: Subject to any disclaimer, the term of this patent is extended or adjusted under 35 U.S.C. 154(b) by 625 days.

(21) Appl. No.: 13/246,941

(22) Filed: Sep. 28, 2011

(65) Prior Publication Data

US 2013/0077737 A1    Mar. 28, 2013

(51) Int. Cl.
*A61B 6/03* (2006.01)
*G01N 23/04* (2006.01)
*A61B 6/00* (2006.01)

(52) U.S. Cl.
CPC .............. *A61B 6/035* (2013.01); *A61B 6/4085* (2013.01); *G01N 23/04* (2013.01); *A61B 6/508* (2013.01)

(58) Field of Classification Search
CPC ...... A61B 6/4085; A61B 6/032; A61B 6/035
USPC ........................................ 378/4–20
See application file for complete search history.

(56) References Cited

U.S. PATENT DOCUMENTS

| | | | |
|---|---|---|---|
| 4,511,801 A * | 4/1985 | Tatham et al. | 250/394 |
| 5,581,591 A * | 12/1996 | Burke | H01J 35/02 378/135 |
| 5,784,428 A * | 7/1998 | Schmidt | 378/4 |
| 8,047,715 B2 * | 11/2011 | Noordhoek | A61B 6/035 378/194 |
| 2007/0165786 A1 * | 7/2007 | Grasser | A61B 6/56 378/194 |
| 2011/0021309 A1 * | 1/2011 | Loeshner | F03D 11/0008 475/348 |
| 2012/0148013 A1 * | 6/2012 | Zhang et al. | 378/4 |
| 2012/0189094 A1 * | 7/2012 | Neushul et al. | 378/19 |

FOREIGN PATENT DOCUMENTS

| | | |
|---|---|---|
| EP | 1092391 | 4/2001 |
| WO | 9522241 | 8/1995 |
| WO | 02065918 | 8/2002 |
| WO | 2011032301 | 3/2011 |

* cited by examiner

*Primary Examiner* — Hoon Song
(74) *Attorney, Agent, or Firm* — Cooper & Dunham LLP

(57) ABSTRACT

A cone beam computed tomography system with a horizontally disposed, cylindrical gantry and a method for its use are provided. The cylindrical gantry includes a rotatable cylindrical frame fixed to a support frame. A cone beam X-ray source and X-ray detector are mounted to the circumference of the cylindrical frame at diametrically opposed positions. The cylindrical frame is actuated to revolve the X-ray source-detector arrangement around a horizontal axis, thereby scanning a recumbent subject positioned in the aperture of the cylindrical frame.

14 Claims, 5 Drawing Sheets

SYSTEM AND METHOD FOR CONE BEAM COMPUTED TOMOGRAPHY

FIELD OF THE INVENTION

The present invention relates generally to cone beam computed tomography (CBCT), and more particularly, to a method and system whereby a cone beam X-ray source and X-ray detectors are arranged for scanning recumbent subjects in a pass-through gantry.

BACKGROUND OF INVENTION

It is known to provide computed tomography (CT) scanning systems with a gantry formed as a centrally apertured disk or drum rotatable within a frame. However, these CT scanners use a two-dimensional fan beam tomography, which is a precursor of three-dimensional CBCT. Fan beam CT scanners are equipped with an array of multiple one-dimensional detector elements that detect a fan-shaped beam of X-rays from a gated radiation source. Three-dimensional image information is acquired by rotating the multi-detector array and X-ray source in a spiral or helical fashion to achieve lateral displacement of the subject and detector array. The need for helical displacement makes gantries for conventional fan beam tomography systems complex and cumbersome.

CBCT systems have numerous advantages over fan beam CT scanners due to their capacity to acquire three-dimensional image data with only a single revolution of the detector-radiation source arrangement. These advantages include reduced scan time, reduced radiation dose and improved image accuracy. State of the art CBCT systems typically employ a C-arm-mounted detector and cone beam X-ray source. The C-arm mount is commonly used in clinical dentistry, for example, to acquire volumetric image information of a patient's head while the patient stands or sits. In contrast to horizontally disposed cylindrical gantry systems, the C-mount does not allow volumetric, total-body scanning. As such, conventional CBCT systems cannot be cost-effectively applied as total body scanners.

SUMMARY OF INVENTION

One object of the present invention is to provide a CBCT system with a mobile, low-cost gantry configured for total body scanning of recumbent subjects. This object is achieved in accordance with the principles of the present invention in a CBCT system having a gantry including a cylindrical frame mounted rotatably within a support frame by rotary bearings. A cone beam X-ray source and at least one X-ray detector are mounted at diametrically opposed positions on the cylindrical frame. Rotational actuation of the cylindrical frame is achieved by a toothed pulley or equivalent structure that is coupled to the outer circumference of the cylinder. A cable winding-unwinding system is provided to guide electrical power and signal cables required for electronic components fixed to the cylindrical frame. Electronic components are disposed on the cylinder so that the rotating masses are balanced, and so that the components are easily accessible for maintenance and repair.

A system according to the invention is designed for limited rotation speed, reduced friction, reduced vibration and low noise. Accordingly, complex ancillary devices for absorbing or reducing disadvantageous noise and vibration, which can impair image quality, may be spared. The disclosed system may be mounted on wheels so that it can be mobile, portable or even self-propelled. The scale of the system may be varied, such that the gantry diameter is adapted to the nature of the radiologic enquiry to be performed. This system has numerous fields of application, including general diagnostic radiology, dentistry, surgery, veterinary medicine and industrial.

In another aspect, the invention is embodied in a method for using a CBCT system comprising a horizontally disposed cylindrical gantry to acquire tomographic images of recumbent subjects.

DETAILED DESCRIPTION OF THE INVENTION

Figure 1A:
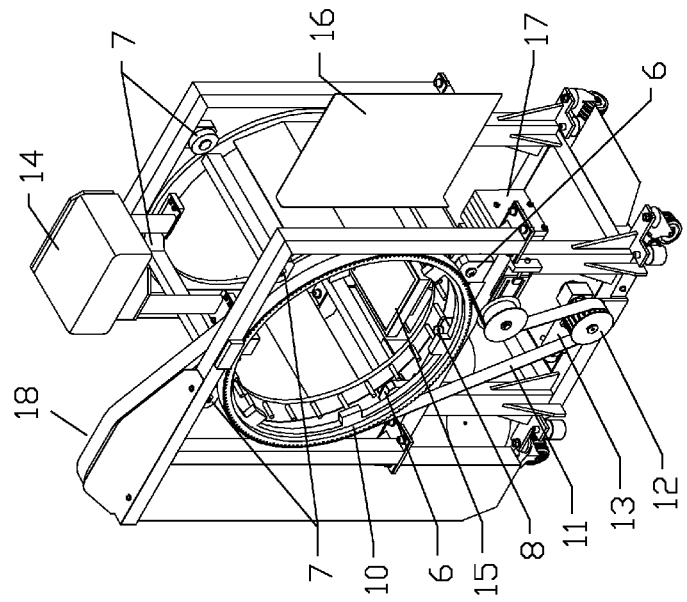
FIG. 1A is a front perspective view of a CBCT system according to an embodiment of the present invention.
Figure 1B:
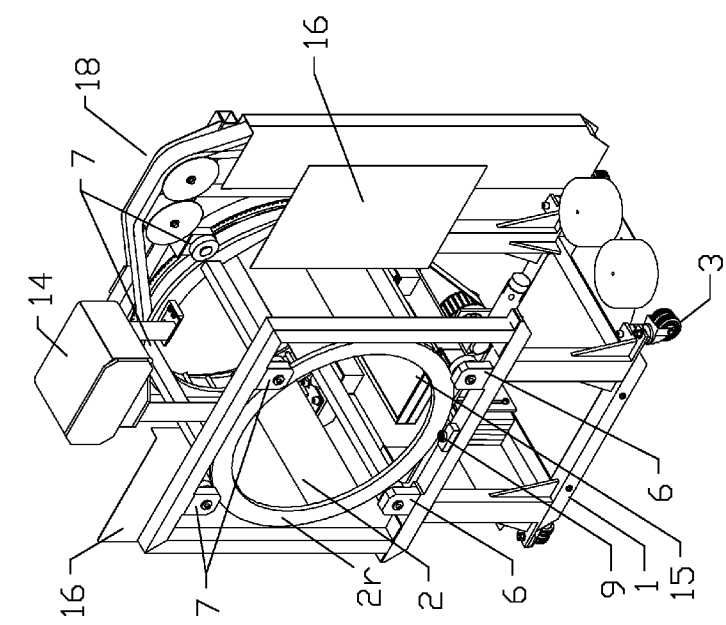
FIG. 1B is a back perspective view of a CBCT system according to an embodiment of the present invention.

FIGS. 1A and 1B show a CBCT system comprising a cylindrical gantry. The cylindrical gantry includes a base frame 1 constructed from welded support beams and supporting a rotatable cylindrical frame 2. Components of the cylindrical frame may be manufactured using known milling and welding techniques. The base frame 1 may stand on a floor surface, fixed or not, or be mounted on wheels 3 as shown in the figures.

Figure 2:
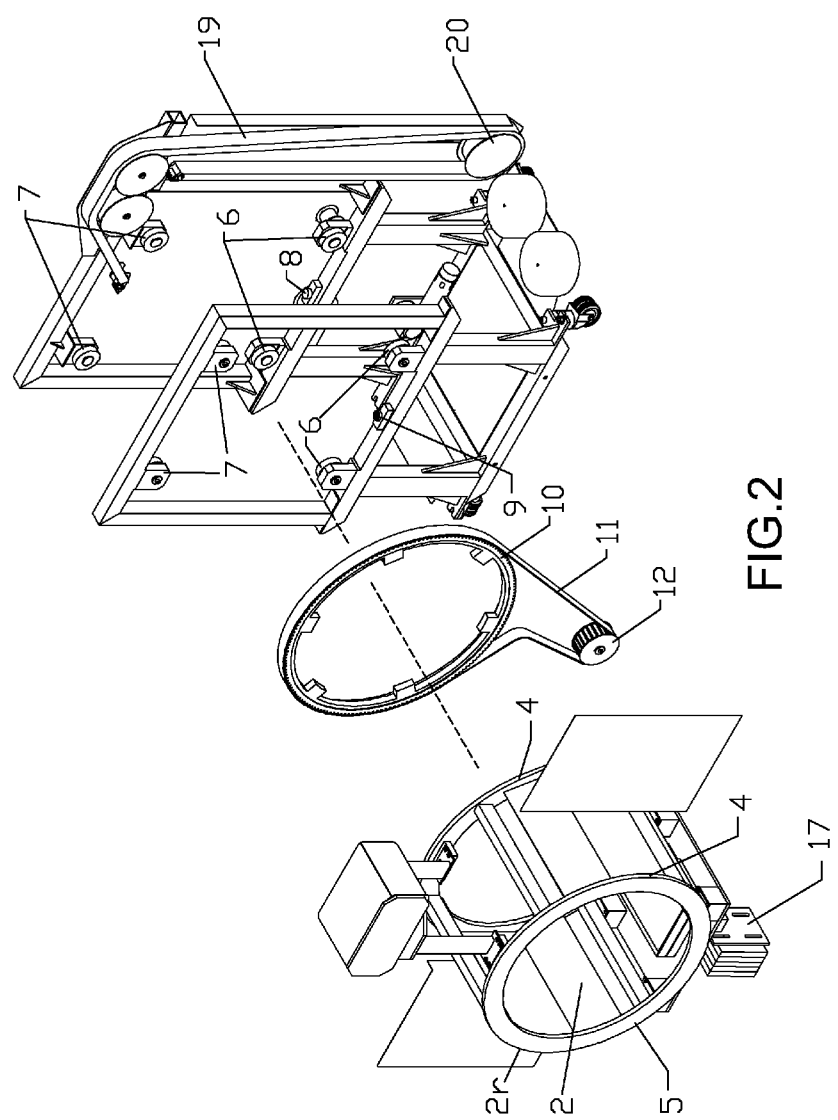
FIG. 2 is an exploded enlarged view of the CBCT system according to an embodiment of the present invention.

As shown in FIG. 2 the cylindrical frame 2 has a horizontal axis of rotation. It includes two rotary circular rails 2r, each having a radial surface-guide 4, and an orthogonal rim surface 5, as axial guide. The axial guides 5 are positioned such that their circular cross-sections are orthogonal to the axis of rotation, and they are parallel to each other. Each rotary circular rail 2r is supported by at least two inferior radial rotary bearings 6 from below, and at least two superior radial rotary bearings 7 from above. The rotary bearings 6 are mounted to the base frame 1. A rear axial rotary bearing 8 and a front axial rotary bearing 9 are on the base frame 1 and apply opposing forces to axial rim surfaces 5 of the cylindrical frame 2 in order to maintain a constant axial position.

Figure 3:
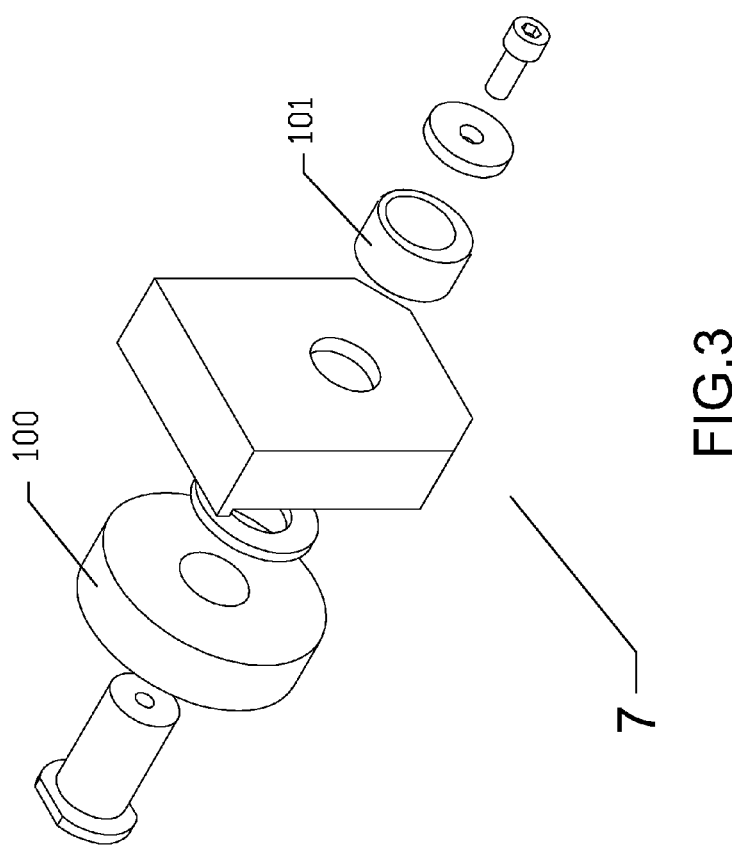
FIG. 3 is an exploded enlarged view of a superior rotary bearing.

As shown in FIG. 3, the bearing roller 100 and eccentric ring 101 of the superior radial bearings 7 are provided to permit radial adjustment of the cylindrical frame 2.

As shown in FIG. 1B, large toothed pulley is mounted to the cylindrical frame 2, and is coupled to a toothed synchronous belt 11. The belt 11 loops around a small toothed pulley 12 that is actuated by a motor 13, thereby enabling rotary actuation of the cylindrical frame 2.

A cone beam X-ray source 14 and at least one X-ray detector 15 are fixed to the cylindrical frame 2 at diametrically opposed positions. Other electronic and electro-mechanic components 16 are positioned on the cylindrical frame 2 such that the weight of all components mounted to the frame 2 is balanced. Counterweights 17, as advantageously shown in FIG. 1B, may be used to achieve this weight balance. In this way, the torque necessary for rotation is minimized and constant. The devices are easily accessible for maintenance and repair.

Additionally, a cable winding-unwinding system 18 comprising a cable carrier 19 and counterweight 20 is provided to manage those cables needed to operate the electronic components mounted to the frame 2. The cable carrier 19 is integral with the base frame 1 at one end, and fixed to a circular rail of the frame 2 at the other end. Signal and power cables are thus wound and unwound during the gantry rotation that occurs during scanning.

Figure 4:
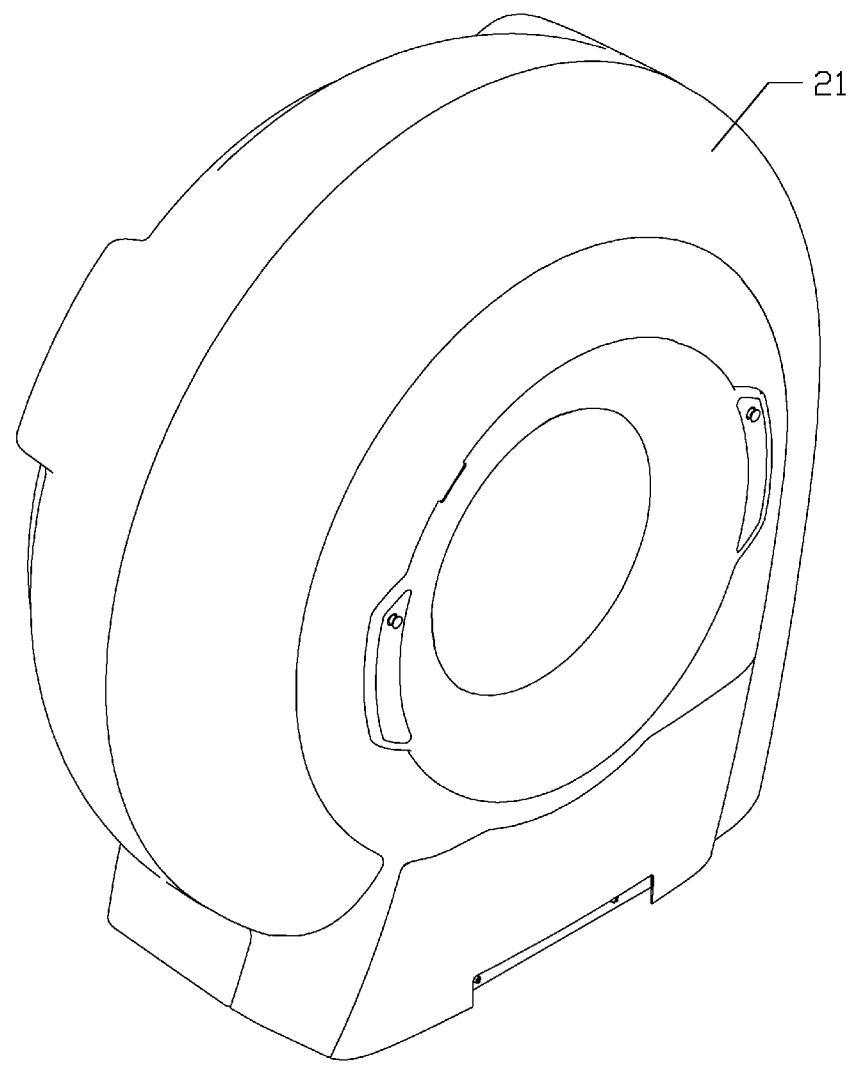
FIG. 4 is an exterior view of a CBCT system according to an embodiment of the present invention.

FIG. 4 shows the cylindrical gantry as enclosed by an exterior housing 21. The housing 21 serves to isolate and protect the gantry components, while providing easy access to those components for maintenance or adjustment.

Figure 5:
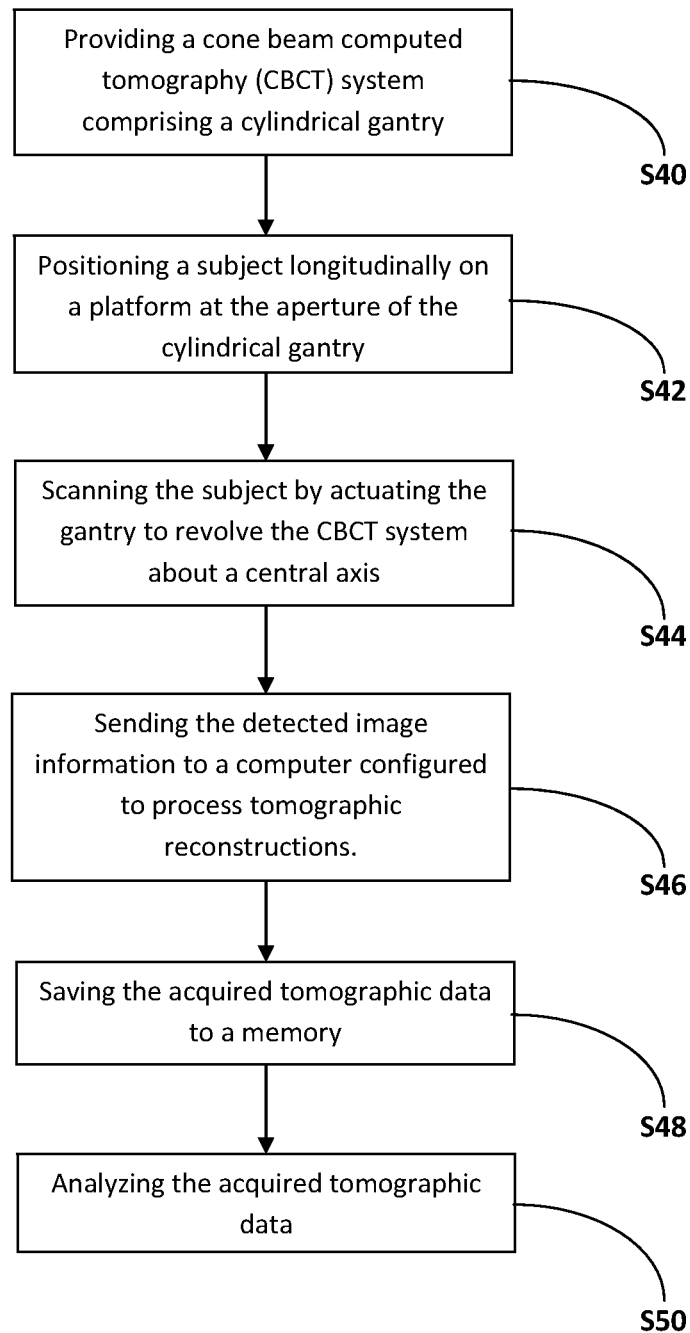
FIG. 5 is a flow chart illustrating a method of acquiring tomographic images of a recumbent subject according to an embodiment of the present invention.

FIG. 5 illustrates a method of using the CBCT system to acquire tomographic data regarding a recumbent subject. A CBCT system comprising a cone beam X-ray source and detector appropriately mounted on a cylindrical gantry is provided (S40). A subject is longitudinally positioned on a platform configured to partially traverse the aperture of the cylindrical gantry (S42). The subject may be a human patient, an animal subject or an inanimate object. A longitudinally positioned human patient may be lying supine or prone on a table (not shown). Once the subject is positioned, the cylindrical gantry operates to revolve the X-ray source 14 and detector 15 about a central axis, scanning the subject (S44). The detector then sends detected image information to a computer configured to process tomographic reconstructions (S46). Subsequently, the computer saves the acquired three-dimensional tomographic datasets to a memory (S48). The tomographic data may be reviewed, analyzed and/or shared by diagnosticians and researchers (S50).

The embodiments set forth in the detailed description and the accompanying figures are described in sufficient detail to enable those skilled in the art to practice the invention. However, the scope of the invention is not limited by the disclosure, and it is to be understood that other embodiments that differ from the pictured and described embodiments may be practiced or utilized without departing from the spirit of the present invention.

What is claimed is:

1. A cone beam computed tomography (CBCT) system for scanning of a subject, comprising:
    a gantry having a rotatable cylindrical frame supported by a base frame, wherein a central rotational axis of the cylindrical frame is substantially horizontal, and a cone beam X-ray source and an X-ray detector are attached to the cylindrical frame,
        wherein the cylindrical frame comprises at least two circular rails, the rails each having a radial surface-guide and an axial surface-guide, and wherein the rails are positioned orthogonal to the axis of rotation and substantially parallel to each other, and
        wherein a plurality of radial rotary bearings and at least, two axial rotary bearings are mounted to the base frame, wherein the radial rotary bearings permit radial adjustment of the cylindrical frame, and wherein the radial and axial rotary bearings rotatably support the cylindrical frame in a constant axial and radial position,
        whereby the CBCT system acquires three-dimensional X-ray tomographic information by scanning the subject in a single revolution of the cylindrical frame; and
    wherein the CBCT system comprises electrical cables and a cable winding-unwinding system fixed to the support frame for winding and unwinding the electrical cables and including a cable carrier and a counterweight.

2. The CBOT system of claim 1, wherein the plurality of radial rotary bearings comprises at least two inferior rotary bearings and at least two superior rotary bearings.

3. The CBCT system of claim 2, wherein the superior rotary bearings permit axial adjustment of the rotary rails.

4. The CBCT system of claim 1 further comprising a synchronous belt coupled to a rotary circular rail and a motor, such that actuation of the belt permits rotation of the rotary rails.

5. The CBCT system of claim 1, wherein the X-ray detector is counterbalanced on the cylindrical frame by an opposed counterweight.

6. The CBCT system of claim 1, wherein the support frame stands permanently, fixed or not, on a floor surface.

7. The CBCT system of claim 1, wherein the support frame is mounted on wheels, mobile, self-propelled or portable.

8. A method of using a CBCT system for scanning of a subject comprising the steps of:
    providing a gantry having a cylindrical frame mounted on a support frame and a substantially horizontal platform positioned at an aperture of the cylindrical frame, wherein an X-ray source and an X-ray detector are fixed to the cylindrical frame at diametrically opposed positions;
        wherein the cylindrical frame comprises at least two circular rails, the rails each having a radial surface-guide and an axial surface-guide, and wherein the rails are positioned orthogonal to the; axis of rotation and substantially parallel to each other, and
        wherein a plurality of radial rotary bearings include a bearing roller and an eccentric ring to permit radial adjustment of the cylindrical frame and wherein the plurality of radial rotary bearings and a plurality of axial rotary bearings rotatably support the rotary circular rails in constant axial and radial positions;
    positioning a subject on the horizontal platform; and
    acquiring three-dimensional X-ray tomographic data by operating the gantry to make a single revolution about the subject.

9. The method of claim 8, wherein the acquired tomographic data relates to dental or maxillofacial structures.

10. The method of claim 8, wherein the acquired tomographic data relates to the body of a human or animal subject.

11. The method of claim 8, wherein the subject is an inanimate object.

12. A method of acquiring three-dimensional tomographic data comprising the steps of
    providing a CECT system according to claim 1;
    scanning a subject by operating the gantry to actuate the cylindrical frame through a single revolution.

13. A method according to claim 12, wherein the subject is a recumbent human.

14. A cone beam computed tomography (CECT) system for scanning of a. subject, comprising:
    a gantry having a. rotatable cylindrical frame supported by a base frame, wherein a central rotational axis of the cylindrical frame is substantially horizontal, and a cone beam X-ray source and an X-ray detector are attached to the cylindrical frame,
        wherein the cylindrical frame comprises at least two circular rails, the rails each having a radial surface-guide and an axial surface-guide, and wherein the rails are positioned orthogonal to the axis of rotation and substantially parallel to each other, and wherein a plurality of radial rotary bearings and at least two axial rotary bearings are mounted to the base frame, wherein the radial rotary bearings include a bearing roller and an eccentric ring to permit radial adjustment of the cylindrical frame, and wherein the radial and axial rotary hearings rotatably support the cylindrical frame in a constant axial and radial position, whereby the CBCT system acquires three-dimensional X-ray tomographic information by scanning the subject in a single revolution of the cylindrical frame.

* * * * *